(12) United States Patent
Schmidt

(10) Patent No.: US 7,468,433 B2
(45) Date of Patent: Dec. 23, 2008

(54) PROCESS FOR THE PRODUCTION OF 16,17-[(CYCLOHEXYLMETHYLEN) BIS(OXY)]-11,21-DIHYDROXY-PREGNA-1,4-DIEN-3,20-DION OR ITS 21-ISOBUTYRAT BY TRANSKETALISATION

(75) Inventor: Beate Schmidt, Allensbach (DE)

(73) Assignee: Nycomed GmbH, Constance (DE)

( * ) Notice: Subject to any disclaimer, the term of this patent is extended or adjusted under 35 U.S.C. 154(b) by 833 days.

(21) Appl. No.: 10/399,689

(22) PCT Filed: Nov. 6, 2001

(86) PCT No.: PCT/EP01/12808

§ 371 (c)(1), (2), (4) Date: Aug. 4, 2003

(87) PCT Pub. No.: WO02/38584

PCT Pub. Date: May 16, 2002

(65) Prior Publication Data

US 2005/0080063 A1    Apr. 14, 2005

(30) Foreign Application Priority Data

Nov. 10, 2000  (EP) .................................. 00124626

(51) Int. Cl.
*C07J 71/00*    (2006.01)

(52) U.S. Cl. ........................................................ 540/63
(58) Field of Classification Search ................... 540/63
See application file for complete search history.

(56) References Cited

U.S. PATENT DOCUMENTS 4,925,933 A * 5/1990 Jakupovic et al. ............. 540/63
5,733,901 A * 3/1998 Gutterer ..................... 514/174

FOREIGN PATENT DOCUMENTS

| DE | 41 29 535 A1 | | 3/1992 |
|---|---|---|---|
| EP | 0 164 636 A2 | | 12/1985 |
| EP | 164636 | * | 12/1985 |
| EP | 0 262 108 A1 | | 3/1988 |
| EP | 0 508 900 A1 | | 10/1992 |
| ES | 527509 | | 8/1985 |
| WO | 94/22899 | | 10/1994 |
| WO | 98/09982 | | 3/1998 |

* cited by examiner

*Primary Examiner*—Barbara P Badio
(74) *Attorney, Agent, or Firm*—The Nath Law Group; Joshua B. Goldberg; Sheldon M. McGee

(57) ABSTRACT

The invention relates to a process for the preparation of 16,17-[(cyclohexylmethylene)bis(oxy)]-11,21-dihydroxypregna-1,4-diene-3,20-dione[11β,16α(R)] and similar compounds, by reaction of an appropriate 16,17-ketal with cyclohexanealdehyde.

5 Claims, No Drawings

PROCESS FOR THE PRODUCTION OF 16,17-[(CYCLOHEXYLMETHYLEN) BIS(OXY)]-11,21-DIHYDROXY-PREGNA-1,4-DIEN-3,20-DION OR ITS 21-ISOBUTYRAT BY TRANSKETALISATION

This application was filed under 35 U.S.C. 371 as a national stage of PCT/EP01/12808, filed Nov. 6, 2001.

TECHNICAL FIELD

The invention relates to a novel process for the preparation of a known glucocorticoid, which is used in the pharmaceutical industry for the production of medicaments.

PRIOR ART

The international patent application WO 9422899 describes novel prednisolone derivatives and a process for their preparation. In this process, 16-hydroxyprednisolone is reacted with cyclohexanealdehyde. German patent application DE 41 29 535 discloses novel glucocorticoids and a process for their preparation. The process comprises reacting pregna-1,4-diene-3,20-dione-16,17-dihydroxy compounds, in the form of their 16,17-diester derivatives, with aldehydes (e.g. with cyclohexanealdehyde) to give the desired final products.

DESCRIPTION OF THE INVENTION

The invention relates to a process for the preparation of the compounds of the formula 1,

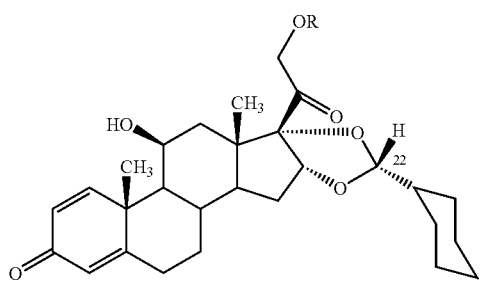

(1)

in which
R is hydrogen (H) or isobutyryl [CO—CH(CH$_3$)$_2$], in predominantly epimerically pure form.

It has now been found that the compounds of the formula 1 are obtained in a simple manner in good yield and surprisingly high epimeric purity when, rather than the 16,17-dihydroxy compound or the 16,17-diester, the corresponding 16,17-ketal, in particular the 16,17-acetonide derivative, is used as a starting material.

The invention thus relates to a process for the preparation of the compounds of the formula 1 in predominantly epimerically pure form, which comprises reacting compounds of the formula 2,

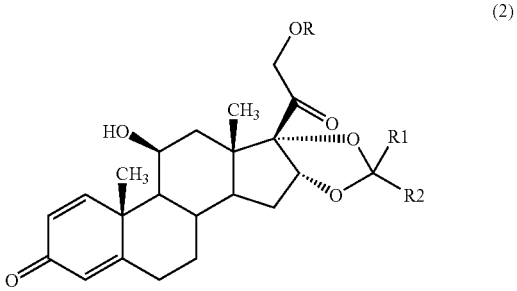

(2)

in which
R is hydrogen (H) or isobutyryl [CO—CH(CH$_3$)$_2$],
R1 is 1-4C-alkyl and
R2 is 1-4C-alkyl,
with cyclohexanealdehyde.

Preferably, the process is carried out using those compounds of the formula 2 in which R1 and R2 are in each case methyl (CH$_3$).

The reaction is carried out in suitable solvents such as, for example, ethers, e.g. dioxane, diisopropyl ether, esters, e.g. ethyl acetate, halogenated hydrocarbons, e.g. methylene chloride, chloroform, nitrated hydrocarbons, e.g. nitromethane, 2-nitropropane or preferably 1-nitropropane, or without solvents, with addition of catalytic or else relatively large amounts of acid, such as mineral acids, e.g. tetrafluoroboric acid or in particular perchloric acid, or sulfonic acids, in particular methanesulfonic acid, at temperatures of advantageously 0° C. to 60° C.

The reaction of the 16-hydroxyprednisolone ketal of the formula 2 with cyclohexanealdehyde normally yields an epimer mixture. Surprisingly, the reaction, however, is controlled according to the invention by means of suitable reaction conditions such that the R-epimer desired and indicated in formula 1 results. According to the invention, "in predominantly epimerically puree form" thus means that the R-epimer (based on the absolute configuration at C-22) in the compound 1 where R=hydrogen (H) results to at least 90%, preferably at least 95%, in particular at least 97%, based on the total yield.

For the predominant preparation of the R-epimer, the following conditions, for example, are preferred: as solvents, halogenated hydrocarbons (such as methylene chloride or chloroform) or nitrated hydrocarbons (such as nitromethane, 2-nitropropane or preferably 1-nitropropane) and, as a catalyst, methanesulfonic acid (at temperatures from 10° C. to 40° C.) or 35-70% strength, in particular 60-70% strength, perchloric acid (at temperatures from 0° C. to 40° C., preferably 15° C. to 30° C., in particular 20° C. to 25° C.).

If the R-epimer is desired in purer form than is achievable on account of the reaction conditions, suitable separation and purification steps—such as, for example, preparative HPLC, or fractional crystallization such as described in international patent application WO 9809982—may follow the reaction.

The following example serves to illustrate the invention in greater detail:

EXAMPLE

16,17-[(Cyclohexylmethylene)bis(oxy)]-11,21-dihydroxypregna-1,4diene-3,20-dione[11β,16α(R)]

20 g of desonide are suspended in 70 ml of 1-nitropropane and treated slowly with ice-cooling with 12.6 ml of 70% strength perchloric acid and 6.6 g of cyclohexanealdehyde. The reaction mixture is stirred overnight at room temperature and then filtered. The filter cake is dissolved in 90 ml of DMF and the solution is added dropwise with stirring to sodium hydrogencarbonate solution. The precipitate is filtered off with suction, washed with water and dried. 19 g of the title compound having an R-/S-epimer ratio of 97.8/2.2 are obtained.

The invention claimed is:

1. A process for the preparation of a compound of the formula 1

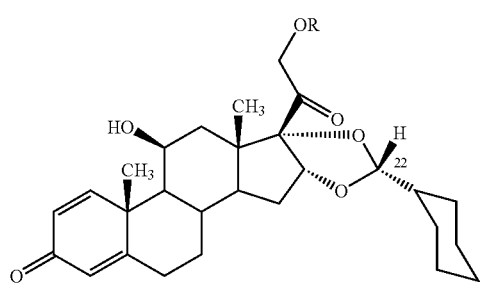

(1)

in which

R is hydrogen (H), in over 95% epimerically pure form, wherein compounds of the formula 2

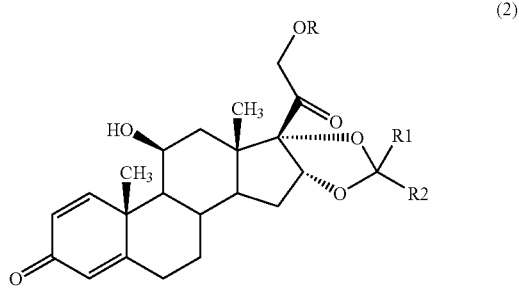

(2)

in which R is hydrogen (H), R1 is methyl (CH3) and R2 is methyl (CH3), are reacted with cyclohexanealdehyde using perchloric acid as a catalyst and a nitrated hydrocarbon as a solvent at a temperature between 0° C. and 40° C.

2. The process as claimed in claim 1, wherein the solvent is nitromethane, 2-nitropropane or 1-nitropropane.

3. The process according to claim 1, wherein the solvent is 1-nitropropane.

4. The process according to claim 1, wherein the perchloric acid is 60% to 70% in strength.

5. The process according to claim 1, wherein the compound of the formula 1 is 16,17-[(Cyclohexylmethylene)bis(oxy)]-11,21-dihydroxypregna-1,4-diene-3,20-diene[11β,16α(R)].

* * * * *

UNITED STATES PATENT AND TRADEMARK OFFICE
CERTIFICATE OF CORRECTION

PATENT NO. : 7,468,433 B2  Page 1 of 1
APPLICATION NO. : 10/399689
DATED : December 23, 2008
INVENTOR(S) : Beate Schmidt It is certified that error appears in the above-identified patent and that said Letters Patent is hereby corrected as shown below:

Claim 5, Column 4, Line 35,

Please delete "11,21-dihydroxypregna-1,4-diene-3,20-diene[11β,16α(R)]."

and replace with

-- 11,21-dihydroxypregna-1,4-diene-3,20-dione[11β,16α(R)]. --

Signed and Sealed this

Twenty-fourth Day of March, 2009

JOHN DOLL
*Acting Director of the United States Patent and Trademark Office*